US008886282B2

(12) United States Patent
Kim et al.

(10) Patent No.: US 8,886,282 B2
(45) Date of Patent: Nov. 11, 2014

(54) SYSTEM AND METHOD FOR MEASURING MAGNETOCARDIOGRAM OF SMALL ANIMAL

(75) Inventors: In Seon Kim, Daejeon (KR); Yong Ho Lee, Daejeon (KR); Ki Woong Kim, Daejeon (KR)

(73) Assignee: Korea Research Institute of Standards and Science, Daejeon (KR)

( * ) Notice: Subject to any disclaimer, the term of this patent is extended or adjusted under 35 U.S.C. 154(b) by 113 days.

(21) Appl. No.: 13/504,873

(22) PCT Filed: Mar. 9, 2010

(86) PCT No.: PCT/KR2010/001470
§ 371 (c)(1),
(2), (4) Date: May 22, 2012

(87) PCT Pub. No.: WO2011/052856
PCT Pub. Date: May 5, 2011

(65) Prior Publication Data
US 2012/0238860 A1    Sep. 20, 2012

(30) Foreign Application Priority Data

Oct. 30, 2009   (KR) .................... 10-2009-0104557

(51) Int. Cl.
| | |
|---|---|
| A61B 5/05 | (2006.01) |
| G01R 33/02 | (2006.01) |
| G01R 33/00 | (2006.01) |
| G01V 3/00 | (2006.01) |
| G01R 33/035 | (2006.01) |
| A61B 5/04 | (2006.01) |

(52) U.S. Cl.
CPC .......... *A61B 5/04007* (2013.01); *A61B 2503/40* (2013.01)
USPC ........... 600/409; 324/248; 324/244; 324/260; 324/261; 324/301; 505/162

(58) Field of Classification Search
USPC .......... 600/409; 324/248, 226, 244, 260, 261, 324/300, 301; 505/162; 327/370
See application file for complete search history.

(56) References Cited

U.S. PATENT DOCUMENTS

| | | | | |
|---|---|---|---|---|
| 5,408,178 | A | * | 4/1995 | Wikswo et al. ............... 324/201 |
| 5,601,081 | A | * | 2/1997 | Tomita et al. ................. 600/409 |
| 7,002,341 | B2 | * | 2/2006 | Baudenbacher et al. ..... 324/248 |

FOREIGN PATENT DOCUMENTS

| | | |
|---|---|---|
| KR | 1998-083826 | 12/1998 |
| KR | 10-0562009 0043413 | 3/2006 |
| KR | 10-2008-0043413 | 5/2008 |

OTHER PUBLICATIONS

Ono et al., "Development of Mice Biomagnetic Measurement System Using dc-SQUID Magnetometer", IEEE Transactions on Applied Superconductivity, vol. 15, No. 2, Jun. 2005, pp. 640-643.*
International Search Report mailed Oct. 28, 2010 for International Patent Application No. PCT/KR2010/001470.

* cited by examiner

*Primary Examiner* — Katherine Fernandez
(74) *Attorney, Agent, or Firm* — Swanson & Bratschun, L.L.C.

(57) ABSTRACT

A system and method for measuring a magnetocardiogram (MCG) in order to measure a weak magnetic field generated from the heart of a small animal such as a laboratory rat are provided. The system includes a case, a SQUID sensor located and fixed inside the case to detect magnetism, a platform arranged near the SQUID sensor inside the case, the small animal being placed on the platform, a linear station to which the platform is fixed to move a location of the platform, and a control unit configured to control operations of the SQUID sensor and the linear station and measure the MCG of the small animal using intensities of the magnetism detected by the SQUID sensor.

4 Claims, 9 Drawing Sheets

SYSTEM AND METHOD FOR MEASURING MAGNETOCARDIOGRAM OF SMALL ANIMAL

CROSS-REFERENCE TO RELATED APPLICATION

This application is a 35 U.S.C. §371 national phase application of PCT/KR2010/001470 (WO 2011/052856), filed on Mar. 9, 2010, entitled "System and Method for Measuring Magnetocardiogram of Small Animal", which application claims priority to and the benefit of Korean Patent Application No. 10-2009-0104557, filed on Oct. 30, 2009, the disclosure of which is incorporated herein by reference in its entirety.

BACKGROUND

1. Field of the Invention

The present invention relates to a system and method for measuring information about a magnetocardiogram (MCG) in order to measure a weak magnetic field generated from a heart of a small animal such as a laboratory rat.

2. Discussion of Related Art

In general, a superconducting quantum interface device (SQUID) is a device using a magnetic flux quantization and Josephson-effect in superconductors, and is used as a highly sensitive sensor having quantum-mechanical measurement sensitivity. A magnetometer using the SQUID is known to the most sensitivity among magnetic sensors developed by humans, and is usually used as a biomagnetic sensor for measuring a weak magnetic field generated from an animal's brain, heart, etc. In particular, in order to prevent sudden death, magnetocardiogram (MCG) devices for measuring the heart-signal of the human body are being developed using the SQUID sensor.

Such an MCG device is intended to obtain information on vector components of the electrical signals of the heart by arranging a plurality of SQUID sensors in the form of a grid and combining the measurement information according to spatial distributions of the SQUID sensors. Accordingly, there are disadvantages in which a large number of SQUID sensors are used and thus a peripheral device is complicated and as the number of SQUID sensors is increased, signal processing is very complicated.

Thus, there is a need to provide an inexpensive device capable of simply measuring an MCG of a small animal such as a laboratory rat.

SUMMARY OF THE INVENTION

The present invention is directed to providing a system and method for measuring a magnetocardiogram (MCG) in which the MCG of a small animal such as a laboratory rat may be measured simply and easily, and the measurement can be embodied inexpensively.

One aspect of the present invention provides a system for measuring an MCG using a SQUID sensor including: a case; the SQUID sensor located and fixed inside the case to detect magnetism; a platform arranged near the SQUID sensor inside the case, the small animal being placed thereon; a linear station configured to fix the platform and to move a location of the platform; and a control unit configured to control operations of the SQUID sensor and the linear station and measure the MCG of the small animal using intensities of the magnetism detected by the SQUID sensor.

The linear station may move the platform in three axial directions X, Y and Z.

In addition, the system may further include a turning station for rotating the platform, wherein the control unit may control an operation of the turning station.

The control unit may be configured to output a control signal to the linear station in order to measure MCGs from a plurality of latticed locations on the platform on which the small animal is placed, detect respective maximum absolute values in one direction and the other direction on the basis of a set X-coordinate from among values of the measured MCGs to calculate a plurality of points on the circumference of a virtual circle having a diameter corresponding to a straight line connecting two points, at set angular intervals from any one of coordinates at which the maximum absolute values are detected, on the circumference of the virtual circle, and sequentially output a plurality of movement control signals to the linear station in order to measure values of the MCGs from the plurality of calculated points on the circumference.

In addition, the system may further include a memory, wherein the control unit may be configured to output a control signal to the linear station in order to measure the MCGs from a plurality of latticed points on the platform on which the small animal is placed, store values of the measured MCGs for respective latticed coordinates in the memory, detect respective maximum absolute values in one direction and the other direction on the basis of a set X-coordinate from among values of the measured MCGs, and load the values of the measured MCGs for the plurality of points on the circumference of a virtual circle having a diameter corresponding to a straight line connecting two points, at set angular intervals from any one of coordinates at which the maximum absolute values are detected, on the circumference of the virtual circle, from the memory to output as information about the MCGs.

The information about the MCG may be obtained from a value of an MCG on the nearest point of the plurality of latticed points when the plurality of points on the circumference of the virtual circle are spaced from the plurality of latticed points.

In addition, the system may further include a sensor movement driving device in order to move the SQUID sensor, wherein the SQUID sensor may be configured to be moved on a horizontal plane, and the control unit is configured to output control signals to the linear station in order to measure the MCGs from a plurality of latticed locations on the platform on which the small animal is placed, detect respective maximum absolute values in one direction and the other direction on the basis of a set X-coordinate from among values of the measured MCGs, output a control signal to the linear station such that a rotation axis of the turning station matches a coordinate of a center point of a straight line connecting two points, output a control signal to the sensor movement driving device such that the SQUID sensor is located on the circumference of a virtual circle having a radius from a rotation center to any one of coordinates at which the maximum absolute values are detected, and output an operation control signal to the turning station in order to rotate at set angular intervals such that the values of the MCGs are specific from a plurality of points on the circumference of a virtual circle.

Another aspect of the present invention provides a method of measuring an MCG of a small animal, including: measuring the MCGs on a plurality of coordinates set for the small animal; detecting coordinates having respective maximum absolute values in one direction and the other direction on the basis of a set X-coordinate from among values of the MCGs measured in the measuring step; and obtaining the MCGs of a plurality of points spaced at set angular intervals on the circumference of a virtual circle having a dimension corresponding to a straight line connecting two coordinates detected in the detecting step.

The measuring step may include a process of storing values of the measured MCGs into a memory, and the detecting step may be performed by loading the values of the MCGs for the plurality of points on the circumference of the virtual circle from the memory.

The obtaining step may include a process of calculating coordinates of the plurality of points spaced at set angular intervals on the circumference of the virtual circle, and a process of measuring the MCG from the calculated coordinates of the plurality of points.

The obtaining step may include a process of matching a center coordinate of the virtual circle with a rotation axis of a platform on which the small animal is placed, a process of placing a SQUID sensor on the circumference of the virtual circle, and a process of measuring the MCG by rotating the platform on which the small animal is placed, at set angular intervals.

BRIEF DESCRIPTION OF THE DRAWINGS

The above and other objects, features and advantages of the present invention will become more apparent to those of ordinary skill in the art by describing in detail exemplary embodiments thereof with reference to the attached drawings, in which:

FIG. 8 is a block diagram for explaining operations of the system for measuring an MCG of a small animal shown in FIGS. 6 and 7; 20 . . . SQUID SENSOR, 70 . . . SENSOR MOVEMENT DRIVING UNIT, 52 . . . ANGLE SENSING UNIT, 50 . . . CONTROL UNIT, 51 . . . MEMORY, 31 . . . LINEAR STATION DRIVING UNIT, 61 . . . TURNING STATION DRIVING UNIT;

FIG. 9 illustrates the measured MCG information of a small animal measured through exemplary embodiments of the present invention.

DETAILED DESCRIPTION OF EXEMPLARY EMBODIMENTS

Hereinafter, exemplary embodiments of the present invention will be described in detail. However, the present invention is not limited to the exemplary embodiments disclosed below, but can be implemented in various forms. The following exemplary embodiments are described in order to enable those of ordinary skill in the art to embody and practice the present invention.

Although the terms first, second, etc. may be used to describe various elements, these elements are not limited by these terms. These terms are only used to distinguish one element from another. For example, a first element could be termed a second element, and, similarly, a second element could be termed a first element, without departing from the scope of exemplary embodiments. The term "and/or" includes any and all combinations of one or more of the associated listed items.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

The terminology used herein is for the purpose of describing particular embodiments only and is not intended to be limiting of exemplary embodiments. The singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements, components and/or groups thereof, but do not preclude the presence or addition of one or more other features, integers, steps, operations, elements, components and/or groups thereof.

With reference to the appended drawings, exemplary embodiments of the present invention will be described in detail below. To aid in understanding the present invention, like numbers refer to like elements throughout the description of the figures, and the description of the same elements will be not reiterated.

Figure 1:
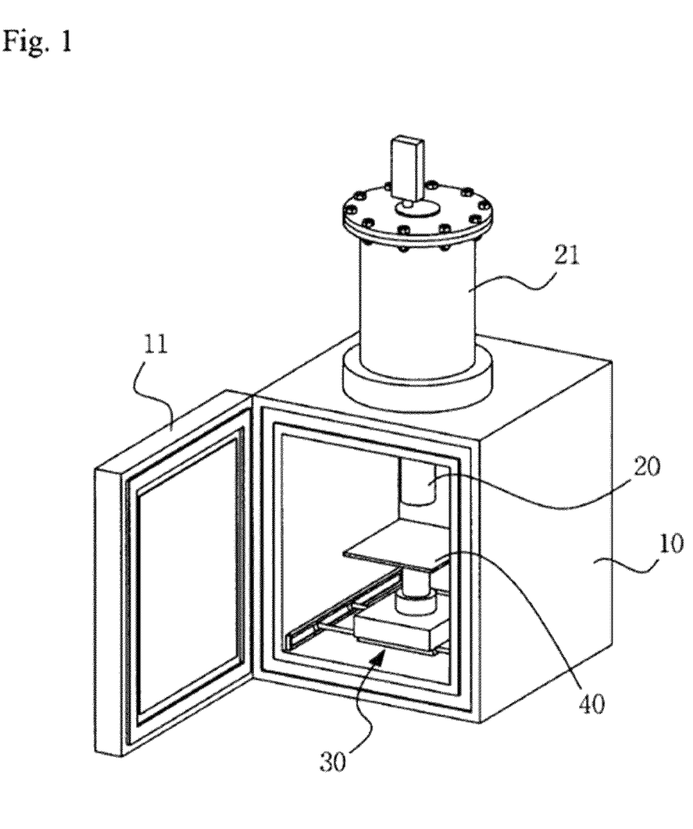
FIG. 1 illustrates a mechanical configuration of a system for measuring a magnetocardiogram (MCG) of a small animal according to an exemplary embodiment of the present invention.
Figure 2:
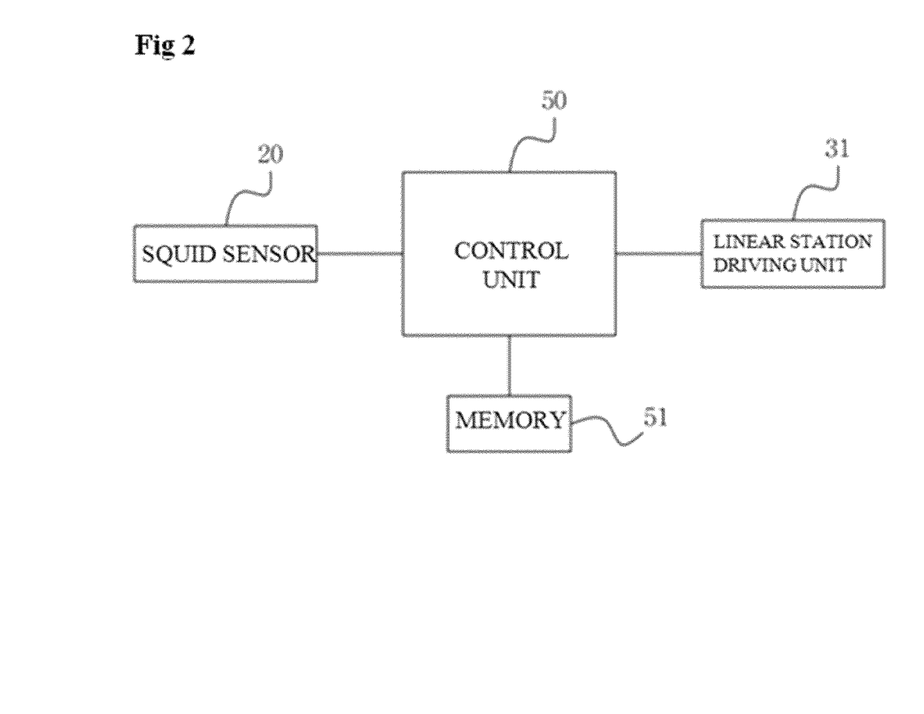
FIG. 2 is a block diagram for explaining operations of the system for measuring an MCG of a small animal according to an exemplary embodiment of the present invention; 20 . . . SQUID SENSOR, 50 . . . CONTROL UNIT, 51 . . . MEMORY, 31 . . . LINEAR STATION DRIVING UNIT.
Figure 3A:
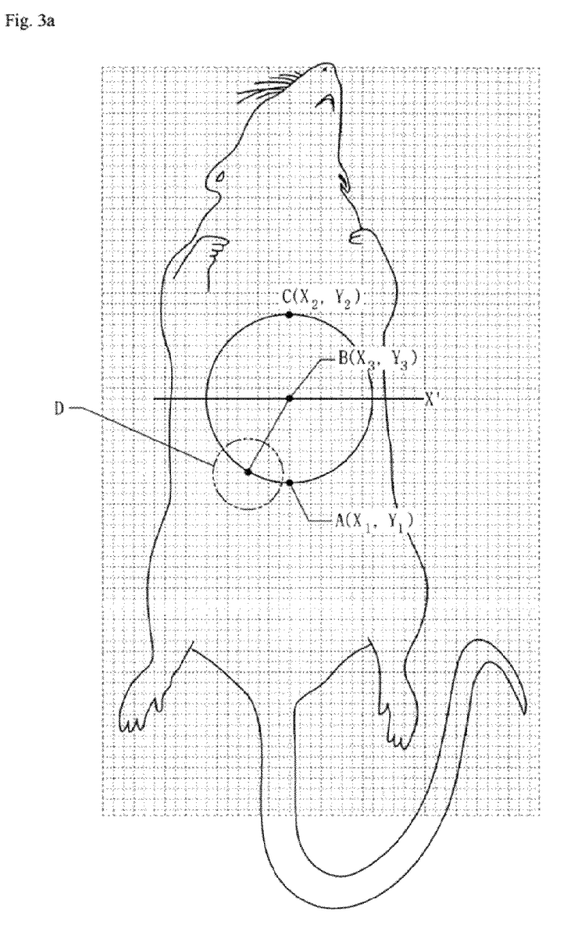
FIGS. 3 to 5 illustrate a method of measuring an MCG of a small animal according to an exemplary embodiment of the present invention.
Figure 3B:
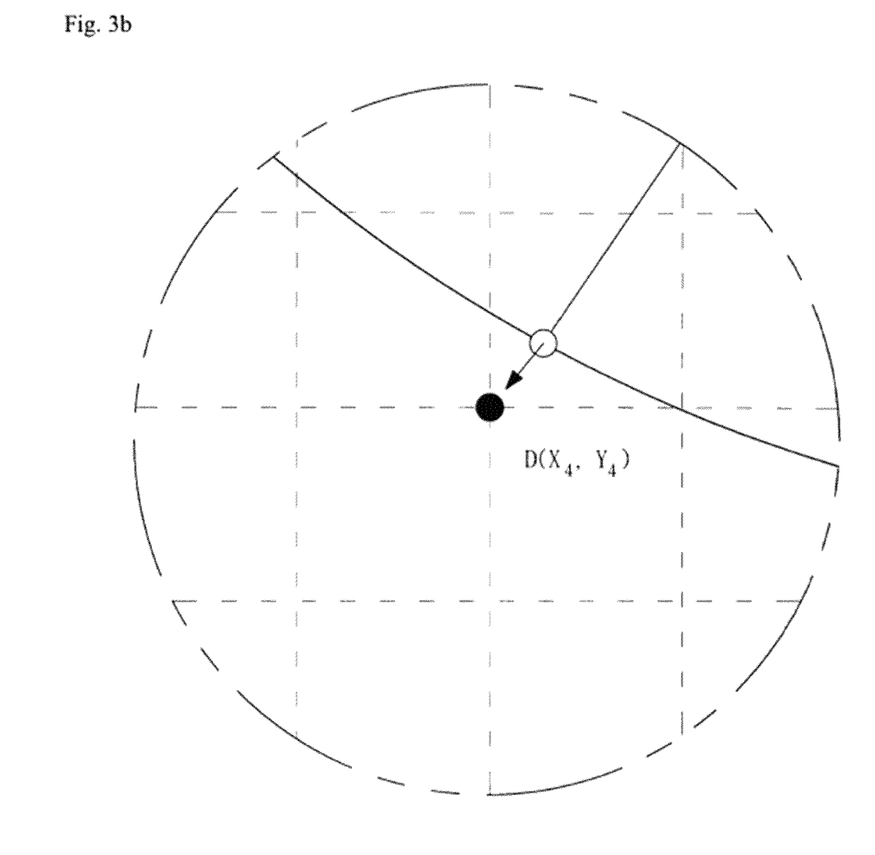
Figure 4:
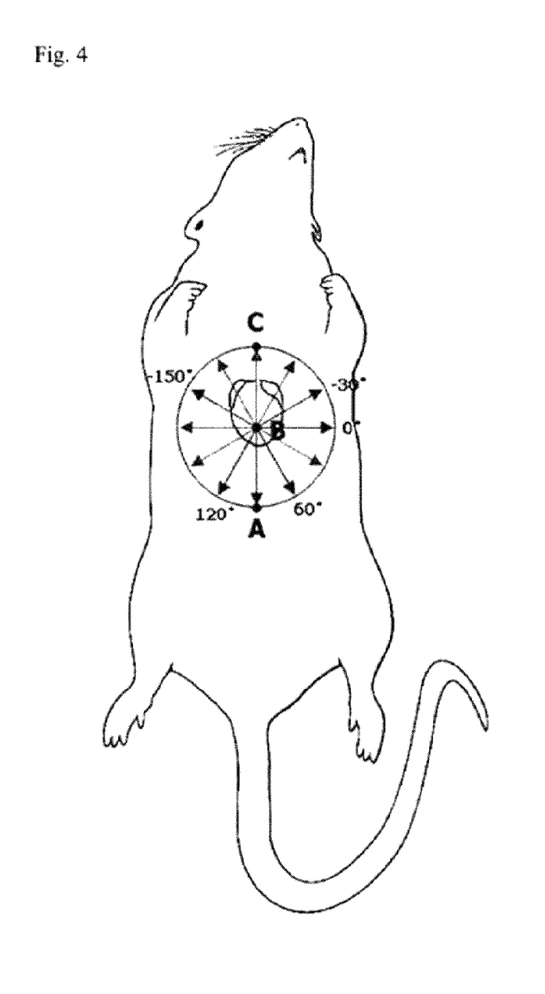
Figure 5:
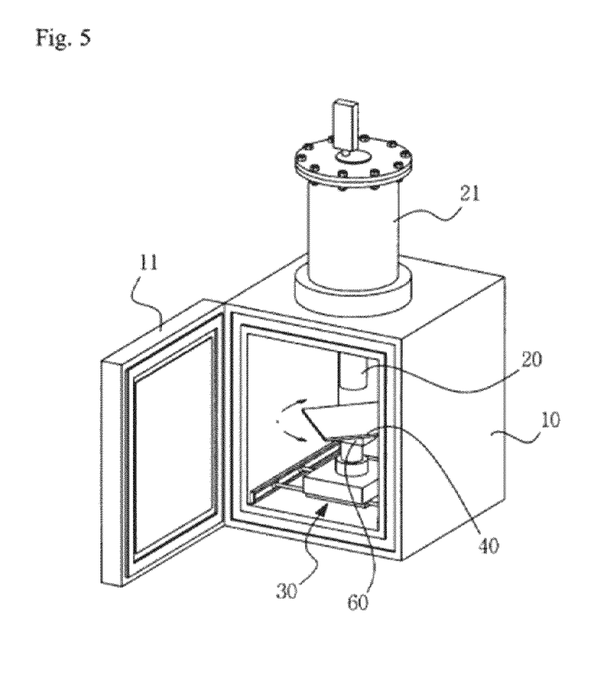
Figure 6:
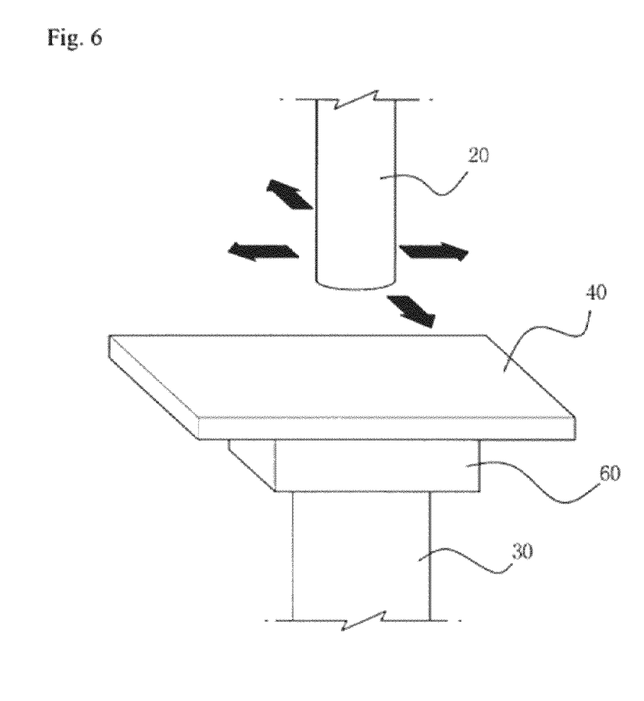
FIG. 6 illustrates a mechanical configuration of a system for measuring an MCG of a small animal according to another exemplary embodiment of the present invention.
Figure 7:
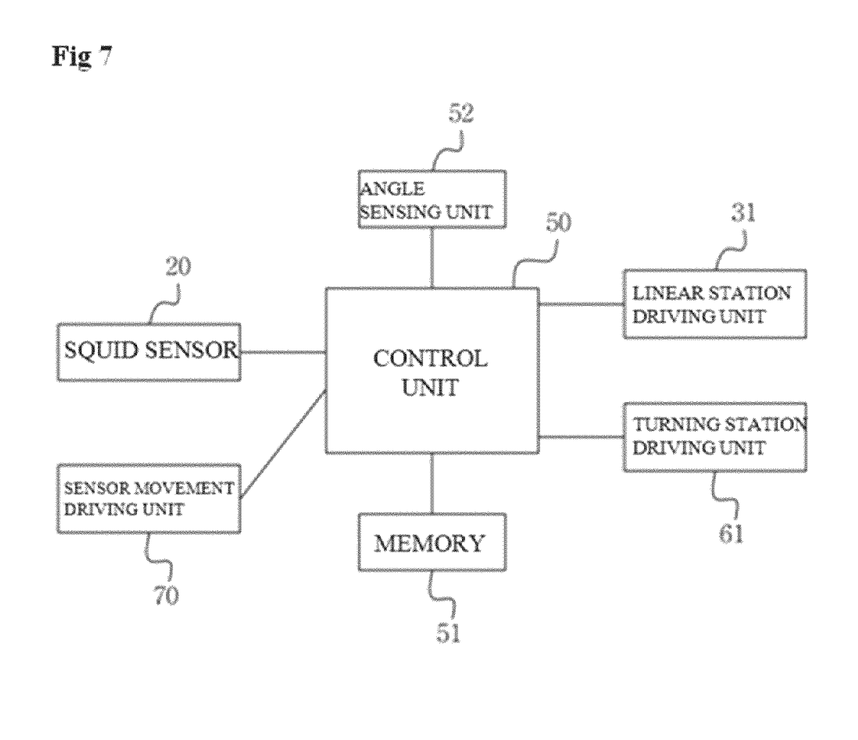
FIG. 7 illustrates an operation of a SQUID sensor shown in FIG. 6.
Figure 8:
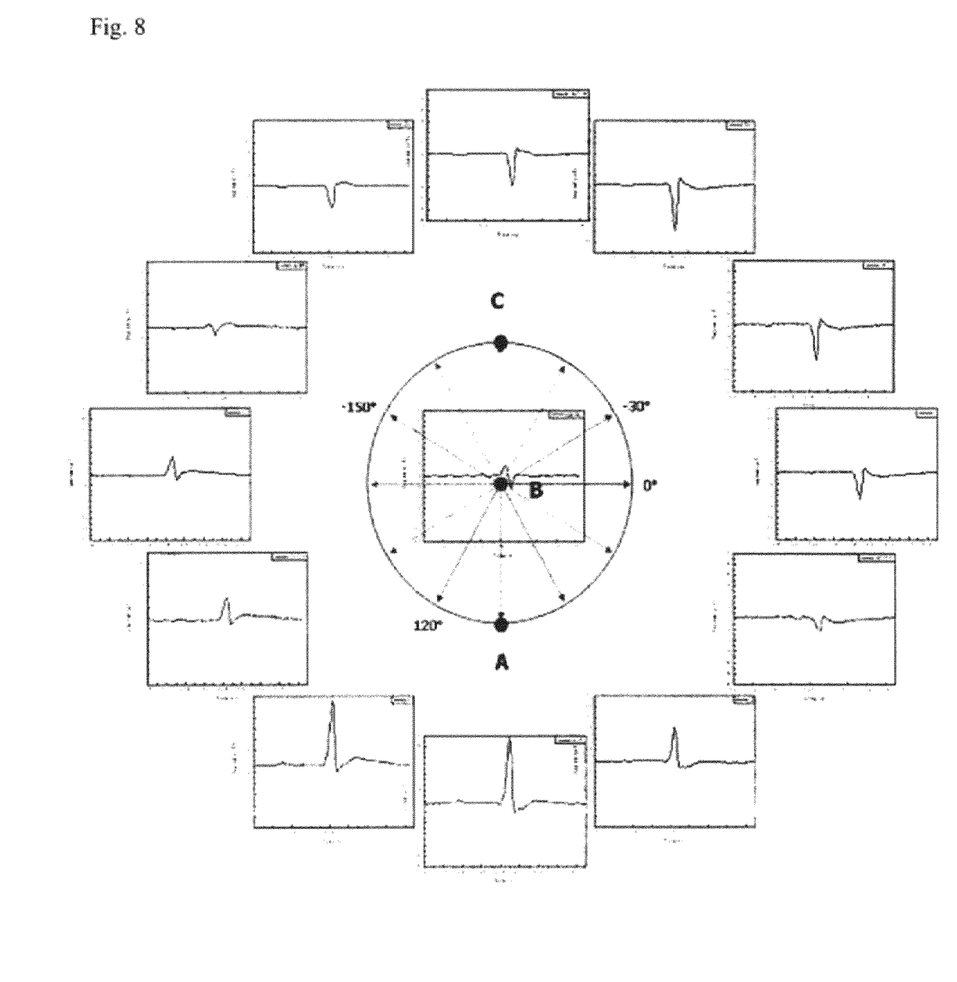

FIG. 1 illustrates a mechanical configuration of a system for measuring a magnetocardiogram (MCG) of a small animal according to an exemplary embodiment of the present invention; FIG. 2 is a block diagram for explaining operations of a system for measuring an MCG of a small animal according to an exemplary embodiment of the present invention; FIGS. 3 to 5 illustrate a method of measuring an MCG of a small animal according to an exemplary embodiment of the present invention; FIG. 6 illustrates a mechanical configuration of a system for measuring an MCG of a small animal according to another exemplary embodiment of the present invention; FIG. 7 illustrates an operation of a SQUID sensor shown in FIG. 6; FIG. 8 is a block diagram for explaining operations of a system for measuring an MCG of a small animal shown in FIGS. 6 and 7; and FIG. 9 illustrates information about MCGs of a small animal measured through exemplary embodiments of the present invention.

As shown in FIG. 1, according to an exemplary embodiment of the present invention, a system for measuring an MCG of a small animal includes a case 10 that has a rectangular shape in which one side thereof is opened and a door 11 is provided on the one opened side to be sealed from the outside thereof when the door 11 is closed, a SQUID sensor 20 located inside the case 10 in order to measure magnetism, a platform 40 arranged near the SQUID sensor 20 inside the case 10, the small animal such as an experimental rat being placed on the platform 40, and a linear station 30 for moving the platform 40 in three directions (X, Y and Z).

The case 10 may include highly conductive metals and highly permeable magnetic materials to shield external magnetism, and the linear station 30 may include a synthetic resin material excluding any metallic material to prevent the disturbance of a magnetic field during operation.

A reference 21 is a cooling tank for cooling the SQUID sensor 20 to maintain a low temperature. A detailed description of the cooling tank 21 will be omitted.

In the system for measuring an MCG of a small animal according to this exemplary embodiment as described above, the measuring of information about MCGs of the small animal may be implemented by various exemplary embodiments. The various exemplary embodiments will be described in detail below.

Embodiment 1

A small animal is placed on the platform 40, and the linear station 30 is moved in the opposite direction of gravity such that the small animal can be placed near the SQUID sensor 20. Subsequently, the linear station 30 is moved in a horizontal planar direction, that is, in directions X and Y, to obtain information about MCGs, which will be described in detail with reference to FIGS. 2 to 5.

The system for measuring the MCG of the small animal according to this exemplary embodiment as described above is controlled by control logics of a control unit 50. The control unit 50 outputs signals for controlling operations of the SQUID sensor 20 and a linear station driving unit 31, and stores sensed values received from the SQUID sensor 20 in a memory 51.

Referring to FIG. 3, virtual grids are provided on the platform 40 on which the small animal is placed, and the control unit 50 outputs control signals to the linear station driving unit 31 and the SQUID sensor 20 in order to obtain values of MCGs for latticed intersecting points. Accordingly, it is possible to measure MCGs at respective intersecting points through movement of the linear station 30. The values with respect to the plurality of latticed intersecting points as described above measured by the SQUID sensor 20 are stored in the memory 51 in addition to coordinates of corresponding intersecting points.

Accordingly, the control unit 50 searches points having respective maximum absolute values in one direction and the other direction on the basis of set X coordinates from among the values stored in the memory 51, and loads and outputs MCGs of points spaced at set angles, for example, at 30° intervals on a virtual circle from the memory 51. In practice, the two points are points detected at the top and bottom of the heart, and the set X coordinate is an X-axial coordinate at which the heart is located.

Referring to FIG. 3, when the maximum absolute values in one direction and the other direction on the basis of set X-axis, that is, X', are detected at points A (X1, Y1) and C (X2, Y2), respectively, values of MCGs of points spaced apart at 30° intervals clockwise from point A on the circumference of a virtual circle having the diameter corresponding to a straight line connecting two points A and B can be loaded and output from the memory 51. At this time, when the points spaced apart 30° clockwise from point A do not correspond to the intersecting points on the virtual grids as shown in FIG. 4, it is preferable to select a point D (X4, Y4) that is the nearest intersecting point as an alternative point for the point that is spaced apart 30°. Thus, the control unit 50 loads a value of the MCG of point D from the memory 51 and outputs the same.

Embodiment 2

In this embodiment, the control unit 50 is configured to obtain a plurality of coordinate points spaced apart at 30° intervals clockwise from the point A on the circumference of the virtual circle in order to measure MCGs of points corresponding to the obtained coordinate values, as in the exemplary embodiment 1. In addition, the control unit 50 is configured to output a control signal to the linear station driving unit 31 to sequentially move the platform 40 to the obtained coordinate points and obtain an MCG of a small animal located on the platform 40 by the linear station 30 from the plurality of coordinate points Embodiment 3

This embodiment will be described with reference to FIGS. 6 to 8.

Referring to FIG. 6, a system according to this embodiment further includes a turning station 60 that rotates the platform 40, in addition to the linear station 30 that moves the platform 40 on which the small animal is placed in three directions X, Y and Z, and a turning station driving unit 61 that drives the turning station 60, unlike the exemplary embodiment shown in FIG. 1. In addition, the SQUID sensor 20 is installed to be moved in a horizontal plan direction, that is, two-dimensionally, and a sensor movement driving unit 70 that moves the SQUID sensor 20 is provided.

When the values of the MCGs for the plurality of points on the circumference of the virtual circle are obtained as in the exemplary embodiments 1 and 2, the control unit 30 adjusts the linear station 30 such that the rotation axis of the turning station 60 matches a center point of the virtual circle and outputs a control signal to the sensor movement driving unit 70 such that the SQUID sensor 20 is located on the circumference of the virtual circle. When the rotation axis of the turning station 60 matches a center point of the virtual circle and the SQUID sensor 20 is located on the circumference of the virtual circle, the control unit 50 outputs a control signal such that the turning station 60 rotates at a set angular intervals, that is, 30° intervals, and the SQUID sensor 20 can measure the MCGs for the respective 30° points.

FIG. 9 shows an example of optimal information about MCGs of a small animal, as described in the exemplary embodiments 1 to 3 above.

Referring to the MCG information shown in FIG. 9, although there may be individual differences in small animals, there is a point at which a signal from the location of the heart appears as a maximum (maximum absolute value) in the direction of the abdomen. In addition, although the sizes of the peak values are different from each other, there is a feature in which a symmetrical waveform is measured. The MCG information as described above is used as a very important data in understanding activities and actions of the heart in the field of medicine.

In practice, when the MCG is manually measured for a small animal such as a laboratory rat, the location of the heart may be point B shown in FIG. 8. In addition, when the location of the heart is moved from point B in the direction of the abdomen by adjusting the locations of X and Y, the location at which the largest signal is measured and detected, and the location may be point A shown in FIG. 9. In addition, when the location of the heart is moved from point B in the direction of the head by adjusting the locations of X and Y, the location at which the largest signal is measured and detected, and the location may be point C shown in FIG. 9. In MCGs of points A and C, it can be seen that the polarities are opposite from each other, and the sizes represent similar values.

The above-described system and method for measuring an MCG of a small animal such as a laboratory rat according to an exemplary embodiment of the present invention can be provided simply and easily, and the measurement can be embodied inexpensively.

While the invention has been shown and described with reference to certain exemplary embodiments thereof, it will be understood by those skilled in the art that various changes in form and details may be made therein without departing from the spirit and scope of the invention as defined by the appended claims.

What is claimed is:

1. A system for measuring a magnetocardiogram (MCG) of a small animal using a SQUID sensor, comprising:
a case;
the SQUID sensor located and fixed inside the case to detect magnetism;
a platform arranged near the SQUID sensor inside the case, the small animal being placed thereon;
a linear station fixed to the platform and configured to move a location of the platform; and
a control unit, wherein the control unit outputs control signals to control operations of the SQUID sensor and the linear station and the control unit measures the MCG of the small animal using intensities of the magnetism detected by the SQUID sensor,
wherein the linear station moves the platform in three axial directions X, Y and Z in response to the one or more control signals output from the control unit,
and wherein the control unit outputs the one or more control signals to the linear station in order to position the platform to measure MCGs from a plurality of latticed locations on the platform on which the small animal is placed, detects respective maximum absolute values in one direction and the other direction on the basis of a set X-coordinate from among values of the measured MCGs, calculates a plurality of points at set angular intervals from any one of the coordinates at which the maximum absolute values are detected on the circumference of a virtual circle having a diameter corresponding to a straight line connecting coordinates of the detected maximum absolute values, and sequentially outputs a plurality of movement control signals to the linear station in order to measure values of the MCGs from the plurality of calculated points on the circumference.

2. A system for measuring a magnetocardiogram (MCG) of a small animal using a SQUID sensor, comprising:
a case;
the SQUID sensor located and fixed inside the case to detect magnetism;
a platform arranged near the SQUID sensor inside the case, the small animal being placed thereon;
a linear station fixed to the platform and configured to move a location of the platform;
a memory; and
a control unit, wherein the control unit outputs control signals to control operations of the SQUID sensor and the linear station and the control unit measures the MCG of the small animal using intensities of the magnetism detected by the SQUID sensor,
wherein the linear station moves the platform in three axial directions X, Y and Z in response to the one or more control signals output from the control unit,
wherein the control unit outputs the one or more control signals to the linear station in order to position the platform to measure the MCGs from a plurality of latticed points on the platform on which the small animal is placed, store values of the MCGs for respective latticed coordinates in the memory, detects respective maximum absolute values in one direction and the other direction on the basis of a set X-coordinate from among values of the measured MCGs, and loads the values of the MCGs for the plurality of points at set angular intervals from any one of coordinates at which the maximum absolute values are detected, on the circumference of the virtual circle having a diameter corresponding to a straight line connecting the coordinates of the detected maximum absolute values, from the memory to output as information about the MCGs.

3. The system of claim 2, wherein a value of an MCG of the plurality of latticed points nearest to the plurality of points on the circumference of the virtual circle is obtained as the information about the MCGs when the plurality of points on the circumference of the virtual circle are spaced from the plurality of latticed points.

4. A system for measuring a magnetocardiogram (MCG) of a small animal using a SQUID sensor, comprising:
a case;
the SQUID sensor located and fixed inside the case to detect magnetism;
a platform arranged near the SQUID sensor inside the case, the small animal being placed thereon;
a linear station fixed to the platform and configured to move a location of the platform;
a turning station for rotating the platform, wherein the control unit controls an operation of the turning station;
a sensor movement driving device in order to move the SQUID sensor; and
a control unit, wherein the control unit outputs control signals to control operations of the SQUID sensor and the linear station and the control unit measures the MCG of the small animal using intensities of the magnetism detected by the SQUID sensor,
wherein the linear station moves the platform in three axial directions X, Y and Z in response to the one or more control signals output from the control unit,
wherein the SQUID sensor is configured to be movable on a horizontal plane, and the control unit outputs the one or more control signals to the linear station in order to position the platform to measure the MCGs from a plurality of latticed locations on the platform on which the small animal is placed, detects respective maximum absolute values in one direction and the other direction on the basis of a set X-coordinate from among values of the measured MCGs, outputs a control signal to the linear station wherein a rotation axis of the turning station matches a coordinate of a center point of a straight line connecting two points, outputs a control signal to the sensor movement driving device wherein the SQUID sensor is located on the circumference of a virtual circle having a radius from a rotation center to any one of coordinates at which the maximum absolute values are detected, and output an operation control signal to the turning station in order to rotate at set angular intervals wherein the values of the MCGs are specific from a plurality of points on the circumference of the virtual circle.

* * * * *